US012612608B2

(12) United States Patent
Rong et al.

(10) Patent No.: US 12,612,608 B2
(45) Date of Patent: Apr. 28, 2026

(54) CONSTRUCTION OF HIGH-FIDELITY CRISPR/ASCPF1 MUTANT AND USES THEREOF

(71) Applicant: SOUTHERN MEDICAL UNIVERSITY, Guangzhou (CN)

(72) Inventors: Zhili Rong, Guangzhou (CN); Ying Lin, Guangzhou (CN); Hongxin Huang, Guangzhou (CN); Lin Shan, Guangzhou (CN)

(73) Assignee: SOUTHERN MEDICAL UNIVERSITY, Guangzhou (CN)

( * ) Notice: Subject to any disclaimer, the term of this patent is extended or adjusted under 35 U.S.C. 154(b) by 1046 days.

(21) Appl. No.: 17/794,263

(22) PCT Filed: Aug. 19, 2019

(86) PCT No.: PCT/CN2019/101439
§ 371 (c)(1),
(2) Date: Jul. 21, 2022

(87) PCT Pub. No.: WO2021/031085
PCT Pub. Date: Feb. 25, 2021

(65) Prior Publication Data
US 2023/0056843 A1 Feb. 23, 2023

(51) Int. Cl.
| | |
|---|---|
| *C12N 9/22* | (2006.01) |
| *C12N 15/11* | (2006.01) |
| *C12N 15/85* | (2006.01) |
| *C12N 15/90* | (2006.01) |

(52) U.S. Cl.
CPC .............. *C12N 9/22* (2013.01); *C12N 15/11* (2013.01); *C12N 15/85* (2013.01); *C12N 15/907* (2013.01); *C12N 2310/20* (2017.05); *C12N 2800/107* (2013.01); *C12N 2800/80* (2013.01)

(58) Field of Classification Search
None
See application file for complete search history.

(56) References Cited

FOREIGN PATENT DOCUMENTS

| | | | |
|---|---|---|---|
| CN | 107312761 A | 11/2017 | |
| CN | 107488649 A | 12/2017 | |
| WO | WO-2017127807 A1 * | 7/2017 | .............. A61P 35/00 |
| WO | 2019118516 A1 | 6/2019 | |

OTHER PUBLICATIONS

Yamano et al., Crystal structure of Cpf1 in complex with guide RNA and target DNA. Cell (2016), 165: 949-962 (Year: 2016).*
Yoshikawa et al., Two basic residues, Lys-107 and Lys-118, of RuvC resolvase are involved in critical contacts with the Holliday junction for its resolution. Genes to Cells (2000), 5: 803-813 (Year: 2000).*
Pietralla et al., Optimizing ErCas12a for efficient gene editing in *Arabidopsis thaliana*. Plant Biotechnology Journal (2024), 22: 401-412 (Year: 2024).*
Alberts et al. (2008), Chapter 3: Proteins, Molecular Biology of the Cell, Garland science, Taylor & Francis Group, LLC (Year: 2008).*
Kipniss et al., Engineering cell sensing and responses using a GPCR-coupled CRISPR-Cas system. Nature Communications (2017), 8: 2212, pp. 1-10 (Year: 2017).*
Kleinstiver et al., High-fidelity CRISPR-Cas9 nucleases with no detectable genome-wide off-target effects. Nature (2016), 529: 490-494 (Year: 2016).*
Luscombe and Thornton, Protein-DNA interactions: amino acid conservation and the effects of mutations on binding specificity. J. Mol. Biol. (2002), 320: 991-1009 (Year: 2002).*
Kleinstiver et al., Engineered CRISPR-Cas12a variants with increased activities and improved targeting ranges for gene, epigenetic and base editing. Nature Biotechnology (2019), 37: 276-282 (Year: 2019).*
Takashi Yamano, et al., Crystal structure of Cpf1 in complex with guide RNA and target DNA, Cell., 2016, pp. 1-23, 165(4).

* cited by examiner

*Primary Examiner* — Catherine Konopka
(74) *Attorney, Agent, or Firm* — Nitin Kaushik

(57) ABSTRACT

A high-fidelity AsCpf1 mutant is obtained by performing a mutation on arginine at position 951 and/or 955 of a AsCpf1 protein amino acid sequence and replacing the same with an amino acid free of forming a hydrogen bond with DNA of a target site; and the amino acid sequence thereof is shown in SEQ ID NOS: 1-3. The encoding gene of the AsCpf1 mutant has a nucleotide sequence as shown in SEQ ID NO: 4 and can be used in the construction of a CRISPR/AsCpf1 gene editing system. A CRISPR/AsCpf1 gene editing system includes a gene encoding a AsCpf1 protein, and the AsCpf1 protein is the AsCpf1 mutant mentioned above. The CRISPR/AsCpf1 gene editing system can be used in lowering an off-target effect of gene editing. The novel AsCpf1 mutant not only retains the gene editing efficiency of wild-type AsCpf1, but also has a higher specificity than the wild-type AsCpf1.

8 Claims, 2 Drawing Sheets

Specification includes a Sequence Listing.

SEQUENCE LISTING

```
<160> NUMBER OF SEQ ID NOS: 30

<210> SEQ ID NO 1
<211> LENGTH: 1352
<212> TYPE: PRT
<213> ORGANISM: Artificial Sequence
<220> FEATURE:
<223> OTHER INFORMATION: The sequence is synthesized

<400> SEQUENCE: 1

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
        130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285
```

```
Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
    675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
```

-continued

```
705                  710                  715                  720

Ile Ser Phe Gln Arg Ile Ala Glu Lys Glu Ile Met Asp Ala Val Glu
                725                  730                  735

Thr Gly Lys Leu Tyr Leu Phe Gln Ile Tyr Asn Lys Asp Phe Ala Lys
            740                  745                  750

Gly His His Gly Lys Pro Asn Leu His Thr Leu Tyr Trp Thr Gly Leu
        755                  760                  765

Phe Ser Pro Glu Asn Leu Ala Lys Thr Ser Ile Lys Leu Asn Gly Gln
    770                  775                  780

Ala Glu Leu Phe Tyr Arg Pro Lys Ser Arg Met Lys Arg Met Ala His
785                  790                  795                  800

Arg Leu Gly Glu Lys Met Leu Asn Lys Lys Leu Lys Asp Gln Lys Thr
                805                  810                  815

Pro Ile Pro Asp Thr Leu Tyr Gln Glu Leu Tyr Asp Tyr Val Asn His
            820                  825                  830

Arg Leu Ser His Asp Leu Ser Asp Glu Ala Arg Ala Leu Leu Pro Asn
        835                  840                  845

Val Ile Thr Lys Glu Val Ser His Glu Ile Ile Lys Asp Arg Arg Phe
    850                  855                  860

Thr Ser Asp Lys Phe Phe Phe His Val Pro Ile Thr Leu Asn Tyr Gln
865                  870                  875                  880

Ala Ala Asn Ser Pro Ser Lys Phe Asn Gln Arg Val Asn Ala Tyr Leu
                885                  890                  895

Lys Glu His Pro Glu Thr Pro Ile Ile Gly Ile Asp Arg Gly Glu Arg
            900                  905                  910

Asn Leu Ile Tyr Ile Thr Val Ile Asp Ser Thr Gly Lys Ile Leu Glu
        915                  920                  925

Gln Arg Ser Leu Asn Thr Ile Gln Gln Phe Asp Tyr Gln Lys Lys Leu
    930                  935                  940

Asp Asn Arg Glu Lys Glu Lys Val Ala Ala Arg Gln Ala Trp Ser Val
945                  950                  955                  960

Val Gly Thr Ile Lys Asp Leu Lys Gln Gly Tyr Leu Ser Gln Val Ile
                965                  970                  975

His Glu Ile Val Asp Leu Met Ile His Tyr Gln Ala Val Val Val Leu
            980                  985                  990

Glu Asn Leu Asn Phe Gly Phe Lys Ser Lys Arg Thr Gly Ile Ala Glu
        995                  1000                 1005

Lys Ala Val Tyr Gln Gln Phe Glu Lys Met Leu Ile Asp Lys Leu
    1010                 1015                 1020

Asn Cys Leu Val Leu Lys Asp Tyr Pro Ala Glu Lys Val Gly Gly
    1025                 1030                 1035

Val Leu Asn Pro Tyr Gln Leu Thr Asp Gln Phe Thr Ser Phe Ala
    1040                 1045                 1050

Lys Met Gly Thr Gln Ser Gly Phe Leu Phe Tyr Val Pro Ala Pro
    1055                 1060                 1065

Tyr Thr Ser Lys Ile Asp Pro Leu Thr Gly Phe Val Asp Pro Phe
    1070                 1075                 1080

Val Trp Lys Thr Ile Lys Asn His Glu Ser Arg Lys His Phe Leu
    1085                 1090                 1095

Glu Gly Phe Asp Phe Leu His Tyr Asp Val Lys Thr Gly Asp Phe
    1100                 1105                 1110

Ile Leu His Phe Lys Met Asn Arg Asn Leu Ser Phe Gln Arg Gly
    1115                 1120                 1125
```

-continued

```
Leu Pro  Gly Phe Met Pro Ala  Trp Asp Ile Val Phe  Glu Lys Asn
    1130             1135              1140

Glu Thr  Gln Phe Asp Ala Lys  Gly Thr Pro Phe Ile  Ala Gly Lys
    1145             1150              1155

Arg Ile  Val Pro Val Ile Glu  Asn His Arg Phe Thr  Gly Arg Tyr
    1160             1165              1170

Arg Asp  Leu Tyr Pro Ala Asn  Glu Leu Ile Ala Leu  Leu Glu Glu
    1175             1180              1185

Lys Gly  Ile Val Phe Arg Asp  Gly Ser Asn Ile Leu  Pro Lys Leu
    1190             1195              1200

Leu Glu  Asn Asp Asp Ser His  Ala Ile Asp Thr Met  Val Ala Leu
    1205             1210              1215

Ile Arg  Ser Val Leu Gln Met  Arg Asn Ser Asn Ala  Ala Thr Gly
    1220             1225              1230

Glu Asp  Tyr Ile Asn Ser Pro  Val Arg Asp Leu Asn  Gly Val Cys
    1235             1240              1245

Phe Asp  Ser Arg Phe Gln Asn  Pro Glu Trp Pro Met  Asp Ala Asp
    1250             1255              1260

Ala Asn  Gly Ala Tyr His Ile  Ala Leu Lys Gly Gln  Leu Leu Leu
    1265             1270              1275

Asn His  Leu Lys Glu Ser Lys  Asp Leu Lys Leu Gln  Asn Gly Ile
    1280             1285              1290

Ser Asn  Gln Asp Trp Leu Ala  Tyr Ile Gln Glu Leu  Arg Asn Lys
    1295             1300              1305

Arg Pro  Ala Ala Thr Lys Lys  Ala Gly Gln Ala Lys  Lys Lys Lys
    1310             1315              1320

Gly Ser  Tyr Pro Tyr Asp Val  Pro Asp Tyr Ala Tyr  Pro Tyr Asp
    1325             1330              1335

Val Pro  Asp Tyr Ala Tyr Pro  Tyr Asp Val Pro Asp  Tyr Ala
    1340             1345              1350
```

<210> SEQ ID NO 2
<211> LENGTH: 1352
<212> TYPE: PRT
<213> ORGANISM: Artificial Sequence
<220> FEATURE:
<223> OTHER INFORMATION: The sequence is synthesized

<400> SEQUENCE: 2

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125
```

-continued

```
Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
    530                 535                 540
```

-continued

```
Asp Val Asn Lys Glu Lys Asn Asn Gly Ala Ile Leu Phe Val Lys Asn
545             550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
        850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Ala Gln Ala Trp Ser Val
945                 950                 955                 960

Val Gly Thr Ile Lys Asp Leu Lys Gln Gly Tyr Leu Ser Gln Val Ile
```

-continued

```
                  965                 970                 975

His Glu Ile Val Asp Leu Met Ile His Tyr Gln Ala Val Val Val Leu
              980                 985                 990

Glu Asn Leu Asn Phe Gly Phe Lys  Ser Lys Arg Thr Gly  Ile Ala Glu
         995                1000                1005

Lys Ala  Val Tyr Gln Gln Phe  Glu Lys Met Leu Ile  Asp Lys Leu
   1010                1015                1020

Asn Cys  Leu Val Leu Lys Asp  Tyr Pro Ala Glu Lys  Val Gly Gly
   1025                1030                1035

Val Leu  Asn Pro Tyr Gln Leu  Thr Asp Gln Phe Thr  Ser Phe Ala
   1040                1045                1050

Lys Met  Gly Thr Gln Ser Gly  Phe Leu Phe Tyr Val  Pro Ala Pro
   1055                1060                1065

Tyr Thr  Ser Lys Ile Asp Pro  Leu Thr Gly Phe Val  Asp Pro Phe
   1070                1075                1080

Val Trp  Lys Thr Ile Lys Asn  His Glu Ser Arg Lys  His Phe Leu
   1085                1090                1095

Glu Gly  Phe Asp Phe Leu His  Tyr Asp Val Lys Thr  Gly Asp Phe
   1100                1105                1110

Ile Leu  His Phe Lys Met Asn  Arg Asn Leu Ser Phe  Gln Arg Gly
   1115                1120                1125

Leu Pro  Gly Phe Met Pro Ala  Trp Asp Ile Val Phe  Glu Lys Asn
   1130                1135                1140

Glu Thr  Gln Phe Asp Ala Lys  Gly Thr Pro Phe Ile  Ala Gly Lys
   1145                1150                1155

Arg Ile  Val Pro Val Ile Glu  Asn His Arg Phe Thr  Gly Arg Tyr
   1160                1165                1170

Arg Asp  Leu Tyr Pro Ala Asn  Glu Leu Ile Ala Leu  Leu Glu Glu
   1175                1180                1185

Lys Gly  Ile Val Phe Arg Asp  Gly Ser Asn Ile Leu  Pro Lys Leu
   1190                1195                1200

Leu Glu  Asn Asp Asp Ser His  Ala Ile Asp Thr Met  Val Ala Leu
   1205                1210                1215

Ile Arg  Ser Val Leu Gln Met  Arg Asn Ser Asn Ala  Ala Thr Gly
   1220                1225                1230

Glu Asp  Tyr Ile Asn Ser Pro  Val Arg Asp Leu Asn  Gly Val Cys
   1235                1240                1245

Phe Asp  Ser Arg Phe Gln Asn  Pro Glu Trp Pro Met  Asp Ala Asp
   1250                1255                1260

Ala Asn  Gly Ala Tyr His Ile  Ala Leu Lys Gly Gln  Leu Leu Leu
   1265                1270                1275

Asn His  Leu Lys Glu Ser Lys  Asp Leu Lys Leu Gln  Asn Gly Ile
   1280                1285                1290

Ser Asn  Gln Asp Trp Leu Ala  Tyr Ile Gln Glu Leu  Arg Asn Lys
   1295                1300                1305

Arg Pro  Ala Ala Thr Lys Lys  Ala Gly Gln Ala Lys  Lys Lys Lys
   1310                1315                1320

Gly Ser  Tyr Pro Tyr Asp Val  Pro Asp Tyr Ala Tyr  Pro Tyr Asp
   1325                1330                1335

Val Pro  Asp Tyr Ala Tyr Pro  Tyr Asp Val Pro Asp  Tyr Ala
   1340                1345                1350
```

<210> SEQ ID NO 3

-continued

```
<211> LENGTH: 1352
<212> TYPE: PRT
<213> ORGANISM: Artificial Sequence
<220> FEATURE:
<223> OTHER INFORMATION: The sequence is synthesized

<400> SEQUENCE: 3

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
    370                 375                 380
```

-continued

```
Leu Arg Asn Ala Leu Tyr Glu Arg Arg Ile Ser Glu Leu Thr Gly Lys
385                 390             395                 400

Ile Thr Lys Ser Ala Lys Glu Lys Val Gln Arg Ser Leu Lys His Glu
                405             410             415

Asp Ile Asn Leu Gln Glu Ile Ile Ser Ala Ala Gly Lys Glu Leu Ser
            420             425             430

Glu Ala Phe Lys Gln Lys Thr Ser Glu Ile Leu Ser His Ala His Ala
        435             440             445

Ala Leu Asp Gln Pro Leu Pro Thr Thr Leu Lys Lys Gln Glu Glu Lys
    450             455             460

Glu Ile Leu Lys Ser Gln Leu Asp Ser Leu Leu Gly Leu Tyr His Leu
465             470             475                 480

Leu Asp Trp Phe Ala Val Asp Glu Ser Asn Glu Val Asp Pro Glu Phe
            485             490             495

Ser Ala Arg Leu Thr Gly Ile Lys Leu Glu Met Glu Pro Ser Leu Ser
            500             505             510

Phe Tyr Asn Lys Ala Arg Asn Tyr Ala Thr Lys Lys Pro Tyr Ser Val
        515             520             525

Glu Lys Phe Lys Leu Asn Phe Gln Met Pro Thr Leu Ala Ser Gly Trp
    530             535             540

Asp Val Asn Lys Glu Lys Asn Asn Gly Ala Ile Leu Phe Val Lys Asn
545             550             555                 560

Gly Leu Tyr Tyr Leu Gly Ile Met Pro Lys Gln Lys Gly Arg Tyr Lys
            565             570             575

Ala Leu Ser Phe Glu Pro Thr Glu Lys Thr Ser Glu Gly Phe Asp Lys
            580             585             590

Met Tyr Tyr Asp Tyr Phe Pro Asp Ala Ala Lys Met Ile Pro Lys Cys
        595             600             605

Ser Thr Gln Leu Lys Ala Val Thr Ala His Phe Gln Thr His Thr Thr
    610             615             620

Pro Ile Leu Leu Ser Asn Asn Phe Ile Glu Pro Leu Glu Ile Thr Lys
625             630             635                 640

Glu Ile Tyr Asp Leu Asn Asn Pro Glu Lys Glu Pro Lys Lys Phe Gln
            645             650             655

Thr Ala Tyr Ala Lys Lys Thr Gly Asp Gln Lys Gly Tyr Arg Glu Ala
            660             665             670

Leu Cys Lys Trp Ile Asp Phe Thr Arg Asp Phe Leu Ser Lys Tyr Thr
        675             680             685

Lys Thr Thr Ser Ile Asp Leu Ser Ser Leu Arg Pro Ser Ser Gln Tyr
    690             695             700

Lys Asp Leu Gly Glu Tyr Tyr Ala Glu Leu Asn Pro Leu Leu Tyr His
705             710             715                 720

Ile Ser Phe Gln Arg Ile Ala Glu Lys Glu Ile Met Asp Ala Val Glu
            725             730             735

Thr Gly Lys Leu Tyr Leu Phe Gln Ile Tyr Asn Lys Asp Phe Ala Lys
            740             745             750

Gly His His Gly Lys Pro Asn Leu His Thr Leu Tyr Trp Thr Gly Leu
        755             760             765

Phe Ser Pro Glu Asn Leu Ala Lys Thr Ser Ile Lys Leu Asn Gly Gln
    770             775             780

Ala Glu Leu Phe Tyr Arg Pro Lys Ser Arg Met Lys Arg Met Ala His
785             790             795                 800
```

-continued

```
Arg Leu Gly Glu Lys Met Leu Asn Lys Lys Leu Lys Asp Gln Lys Thr
                805             810             815

Pro Ile Pro Asp Thr Leu Tyr Gln Glu Leu Tyr Asp Tyr Val Asn His
            820             825             830

Arg Leu Ser His Asp Leu Ser Asp Glu Ala Arg Ala Leu Leu Pro Asn
        835             840             845

Val Ile Thr Lys Glu Val Ser His Glu Ile Ile Lys Asp Arg Arg Phe
    850             855             860

Thr Ser Asp Lys Phe Phe Phe His Val Pro Ile Thr Leu Asn Tyr Gln
865             870             875             880

Ala Ala Asn Ser Pro Ser Lys Phe Asn Gln Arg Val Asn Ala Tyr Leu
            885             890             895

Lys Glu His Pro Glu Thr Pro Ile Ile Gly Ile Asp Arg Gly Glu Arg
            900             905             910

Asn Leu Ile Tyr Ile Thr Val Ile Asp Ser Thr Gly Lys Ile Leu Glu
            915             920             925

Gln Arg Ser Leu Asn Thr Ile Gln Gln Phe Asp Tyr Gln Lys Lys Leu
    930             935             940

Asp Asn Arg Glu Lys Glu Lys Val Ala Ala Ala Gln Ala Trp Ser Val
945             950             955             960

Val Gly Thr Ile Lys Asp Leu Lys Gln Gly Tyr Leu Ser Gln Val Ile
            965             970             975

His Glu Ile Val Asp Leu Met Ile His Tyr Gln Ala Val Val Val Leu
            980             985             990

Glu Asn Leu Asn Phe Gly Phe Lys Ser Lys Arg Thr Gly Ile Ala Glu
            995             1000            1005

Lys Ala Val Tyr Gln Gln Phe Glu Lys Met Leu Ile Asp Lys Leu
    1010            1015            1020

Asn Cys Leu Val Leu Lys Asp Tyr Pro Ala Glu Lys Val Gly Gly
    1025            1030            1035

Val Leu Asn Pro Tyr Gln Leu Thr Asp Gln Phe Thr Ser Phe Ala
    1040            1045            1050

Lys Met Gly Thr Gln Ser Gly Phe Leu Phe Tyr Val Pro Ala Pro
    1055            1060            1065

Tyr Thr Ser Lys Ile Asp Pro Leu Thr Gly Phe Val Asp Pro Phe
    1070            1075            1080

Val Trp Lys Thr Ile Lys Asn His Glu Ser Arg Lys His Phe Leu
    1085            1090            1095

Glu Gly Phe Asp Phe Leu His Tyr Asp Val Lys Thr Gly Asp Phe
    1100            1105            1110

Ile Leu His Phe Lys Met Asn Arg Asn Leu Ser Phe Gln Arg Gly
    1115            1120            1125

Leu Pro Gly Phe Met Pro Ala Trp Asp Ile Val Phe Glu Lys Asn
    1130            1135            1140

Glu Thr Gln Phe Asp Ala Lys Gly Thr Pro Phe Ile Ala Gly Lys
    1145            1150            1155

Arg Ile Val Pro Val Ile Glu Asn His Arg Phe Thr Gly Arg Tyr
    1160            1165            1170

Arg Asp Leu Tyr Pro Ala Asn Glu Leu Ile Ala Leu Leu Glu Glu
    1175            1180            1185

Lys Gly Ile Val Phe Arg Asp Gly Ser Asn Ile Leu Pro Lys Leu
    1190            1195            1200

Leu Glu Asn Asp Asp Ser His Ala Ile Asp Thr Met Val Ala Leu
```

-continued

```
                   1205             1210             1215

Ile Arg  Ser Val Leu Gln Met  Arg Asn Ser Asn Ala  Ala Thr Gly
    1220             1225             1230

Glu Asp  Tyr Ile Asn Ser Pro  Val Arg Asp Leu Asn  Gly Val Cys
    1235             1240             1245

Phe Asp  Ser Arg Phe Gln Asn  Pro Glu Trp Pro Met  Asp Ala Asp
    1250             1255             1260

Ala Asn  Gly Ala Tyr His Ile  Ala Leu Lys Gly Gln  Leu Leu Leu
    1265             1270             1275

Asn His  Leu Lys Glu Ser Lys  Asp Leu Lys Leu Gln  Asn Gly Ile
    1280             1285             1290

Ser Asn  Gln Asp Trp Leu Ala  Tyr Ile Gln Glu Leu  Arg Asn Lys
    1295             1300             1305

Arg Pro  Ala Ala Thr Lys Lys  Ala Gly Gln Ala Lys  Lys Lys Lys
    1310             1315             1320

Gly Ser  Tyr Pro Tyr Asp Val  Pro Asp Tyr Ala Tyr  Pro Tyr Asp
    1325             1330             1335

Val Pro  Asp Tyr Ala Tyr Pro  Tyr Asp Val Pro Asp  Tyr Ala
    1340             1345             1350

<210> SEQ ID NO 4
<211> LENGTH: 4059
<212> TYPE: DNA
<213> ORGANISM: Artificial Sequence
<220> FEATURE:
<223> OTHER INFORMATION: The sequence is synthesized

<400> SEQUENCE: 4
atgacacagt tcgagggctt taccaacctg tatcaggtga gcaagacact gcggtttgag      60
ctgatcccac agggcaagac cctgaagcac atccaggagc agggcttcat cgaggaggac     120
aaggcccgca atgatcacta caaggagctg aagcccatca tcgatcggat ctacaagacc     180
tatgccgacc agtgcctgca gctggtgcag ctggattggg agaacctgag cgccgccatc     240
gactcctata gaaaggagaa aaccgaggag acaaggaacg ccctgatcga ggagcaggcc     300
acatatcgca atgccatcca cgactacttc atcggccgga cagacaacct gaccgatgcc     360
atcaataaga gacacgccga gatctacaag ggcctgttca aggccgagct gtttaatggc     420
aaggtgctga gcagctggg caccgtgacc acaaccgagc acgagaacgc cctgctgcgg      480
agcttcgaca gtttacaac ctacttctcc ggctttatg agaacaggaa gaacgtgttc       540
agcgccgagg atatcagcac agccatccca caccgcatcg tgcaggacaa cttccccaag     600
tttaaggaga attgtcacat cttcacacgc ctgatcaccg ccgtgccag cctgcgggag      660 cactttgaga acgtgaagaa ggccatcggc atcttcgtga gcacctccat cgaggaggtg     720
ttttccttcc cttttataa ccagctgctg acacagaccc agatcgacct gtataaccag      780
ctgctgggag aatctctcg ggaggcaggc accgagaaga tcaagggcct gaacgaggtg      840
ctgaatctgg ccatccagaa gaatgatgag acagcccaca tcatcgcctc cctgccacac     900
agattcatcc ccctgtttaa gcagatcctg tccgatagga cacccctgtc tttcatcctg     960
gaggagttta gagcgacga ggaagtgatc cagtccttct gcaagtacaa gacactgctg      1020
agaaacgaga acgtgctgga gacagccgag gccctgttta cgagctgaa cagcatcgac      1080 ctgacacaca tcttcatcag ccacaagaag ctggagacaa tcagcagcgc cctgtgcgac     1140
cactgggata cactgaggaa tgccctgtat gagcggagaa tctccgagct gacaggcaag     1200
```

-continued

```
atcaccaagt ctgccaagga gaaggtgcag cgcagcctga agcacgagga tatcaacctg    1260
caggagatca tctctgccgc aggcaaggag ctgagcgagg ccttcaagca gaaaaccagc    1320
gagatcctgt cccacgcaca cgccgccctg gatcagccac tgcctacaac cctgaagaag    1380
caggaggaga aggagatcct gaagtctcag ctggacagcc tgctgggcct gtaccacctg    1440
ctggactggt ttgccgtgga tgagtccaac gaggtggacc ccgagttctc tgcccggctg    1500
accggcatca agctggagat ggagccttct ctgagcttct acaacaaggc cagaaattat    1560
gccaccaaga agccctactc cgtggagaag ttcaagctga actttcagat gcctacactg    1620
gcctctggct gggacgtgaa taaggagaag aacaatggcg ccatcctgtt tgtgaagaac    1680
ggcctgtact atctgggcat catgccaaag cagaagggca ggtataaggc cctgagcttc    1740
gagcccacag agaaaaccag cgagggcttt gataagatgt actatgacta cttccctgat    1800
gccgccaaga tgatcccaaa gtgcagcacc cagctgaagg ccgtgacagc ccactttcag    1860
acccacacaa cccccatcct gctgtccaac aatttcatcg agcctctgga gatcacaaag    1920
gagatctacg acctgaacaa tcctgagaag gagccaaaga agtttcagac agcctacgcc    1980
aagaaaaccg gcgaccagaa gggctacaga gaggccctgt gcaagtggat cgacttcaca    2040
agggattttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag aaggtggcgg ccgctcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240
gaccccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
```

-continued

```
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg gccagctgct gctgaatcac    3840
ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg gatcctaccc atacgatgtt ccagattacg cttatcccta cgacgtgcct    4020
gattatgcat acccatacga tgtccccgac tatgcctga                          4059

<210> SEQ ID NO 5
<211> LENGTH: 9485
<212> TYPE: DNA
<213> ORGANISM: Artificial Sequence
<220> FEATURE:
<223> OTHER INFORMATION: The sequence is synthesized

<400> SEQUENCE: 5
aattgaaggt cgggcaggaa gagggcctat ttcccatgat tccttcatat ttgcatatac      60
gatacaaggc tgttagagag ataattagaa ttaatttgac tgtaaacaca aagatattag     120
tacaaaatac gtgacgtaga aagtaataat ttcttgggta gtttgcagtt ttaaaattat     180
gttttaaaat ggactatcat atgcttaccg taacttgaaa gtatttcgat ttcttggctt     240
tatatatctt gtggaaagga cgaaacaccg taatttctac tcttgtagat atcaccgcct     300
acgtcagtac ctacaagctt tttttacgcg ttgacattga ttattgacta gttattaata     360
gtaatcaatt acggggtcat tagttcatag cccatatatg gagttccgcg ttacataact     420
tacggtaaat ggcccgcctg gctgaccgcc caacgacccc cgcccattga cgtcaataat     480
gacgtatgtt cccatagtaa cgccaatagg gactttccat tgacgtcaat gggtggacta     540
tttacggtaa actgcccact tggcagtaca tcaagtgtat catatgccaa gtacgccccc     600
tattgacgtc aatgacggta aatggcccgc ctggcattat gcccagtaca tgaccttatg     660
ggactttcct acttggcagt acatctacgt attagtcatc gctattacca tgggtcgagg     720
tgagccccac gttctgcttc actctcccca tctcccccccc ctccccaccc caattttgt     780 atttatttat tttttaatta ttttgtgcag cgatggggg ggggggggg ggggcgcgcg       840 ccaggcgggg cggggcgggg cgaggggcgg ggcggggcga ggcggagagg tgcggcggca     900
gccaatcaga gcggcgcgct ccgaaagttt cctttttatgg cgaggcggcg gcggcggcg     960 ccctataaaa agcgaagcgc gcggcgggcg ggagtcgctg cgttgccttc gccccgtgcc    1020
ccgctccgcg ccgcctcgcg ccgcccgccc cggctctgac tgaccgcgtt actcccacag    1080
gtgagcgggc gggacggccc ttctcctccg ggctgtaatt agcgcttggt ttaatgacgg    1140
ctcgtttctt ttctgtggct gcgtgaaagc cttaaagggc tccgggaggg ccctttgtgc    1200 ggggggggagc ggctcggggg gtgcgtgcgt gtgtgtgtgc gtggggagcg ccgcgtgcgg    1260
cccgcgctgc ccggcggctg tgagcgctgc gggcgcggcg cggggctttg tgcgctccgc    1320
gtgtgcgcga ggggagcgcg gccgggggcg gtgccccgcg gtgcgggggg gctgcgaggg    1380
gaacaaaggc tgcgtgcggg gtgtgtgcgt ggggggggtga gcaggggggtg tgggcgcggc    1440 ggtcgggctg taaccccccc ctgcaccccc ctccccgagt tgctgagcac ggcccggctt    1500
cgggtgcggg gctccgtacg gggcgtggcg cggggctcgc cgtgccgggc gggggggtggc    1560
```

-continued

```
ggcaggtggg ggtgccgggc ggggcggggc cgcctcgggc cggggagggc tcggggagg       1620 ggcgcggcgg cccccggagc gccggcggct gtcgaggcgc ggcgagccgc agccattgcc       1680
ttttatggta atcgtgcgag agggcgcagg gacttccttt gtcccaaatc tgtgcggagc       1740
cgaaatctgg gaggcgccgc cgcacccccct ctagcgggcg cggggcgaag cggtgcggcg       1800
ccggcaggaa ggaaatgggc ggggagggcc ttcgtgcgtc gccgcgccgc cgtcccctctc       1860 tccatctcca gcctcggggc tgtccgcagg gggacggctg ccttcggggg ggacggggca       1920 gggcgggggtt cggcttctgg cgtgtgaccg gcggctctag tgcctctgct aaccatgttc       1980
atgccttctt cttttttccta cagctcctgg gcaacgtgct ggttattgtg ctgtctcatc       2040
attttggcaa agaattcatt taggtgacac tatagataat acgactcact ataggggatga       2100 cacagttcga gggctttacc aacctgtatc aggtgagcaa gacactgcgg tttgagctga       2160
tcccacaggg caagaccctg aagcacatcc aggagcaggg cttcatcgag gaggacaagg       2220
cccgcaatga tcactacaag gagctgaagc ccatcatcga tcggatctac aagacctatg       2280
ccgaccagtg cctgcagctg gtgcagctgg attgggagaa cctgagcgcc gccatcgact       2340
cctatagaaa ggagaaaacc gaggagacaa ggaacgccct gatcgaggag caggccacat       2400
atcgcaatgc catccacgac tacttcatcg gccggacaga caacctgacc gatgccatca       2460
ataagagaca cgccgagatc tacaagggcc tgttcaaggc cgagctgttt aatggcaagg       2520
tgctgaagca gctgggcacc gtgaccacaa ccgagcacga gaacgccctg ctgcggagct       2580
tcgacaagtt tacaacctac ttctccggct tttatgagaa caggaagaac gtgttcagcg       2640
ccgaggatat cagcacagcc atcccacacc gcatcgtgca ggacaacttc cccaagttta       2700
aggagaattg tcacatcttc acacgcctga tcaccgccgt gcccagcctg cgggagcact       2760
ttgagaacgt gaagaaggcc atcggcatct tcgtgagcac ctccatcgag gaggtgtttt       2820
ccttcccttt ttataaccag ctgctgacac agacccagat cgacctgtat aaccagctgc       2880
tgggaggaat ctctcgggag gcaggcaccg agaagatcaa gggcctgaac gaggtgctga       2940
atctggccat ccagaagaat gatgagacag cccacatcat cgcctccctg ccacacagat       3000 tcatcccccct gtttaagcag atcctgtccg ataggaacac cctgtctttc atcctggagg       3060
agtttaagag cgacgaggaa gtgatccagt ccttctgcaa gtacaagaca ctgctgagaa       3120
acgagaacgt gctggagaca gccgaggccc tgtttaacga gctgaacagc atcgacctga       3180
cacacatctt catcagccac aagaagctgg agacaatcag cagcgccctg tgcgaccact       3240
gggatacact gaggaatgcc ctgtatgagc ggagaatctc cgagctgaca ggcaagatca       3300
ccaagtctgc caaggagaag gtgcagcgca gcctgaagca cgaggatatc aacctgcagg       3360
agatcatctc tgccgcaggc aaggagctga gcgaggcctt caagcagaaa accagcgaga       3420
tcctgtccca cgcacacgcc gccctggatc agccactgcc tacaaccctg aagaagcagg       3480
aggagaagga gatcctgaag tctcagctgg acagcctgct gggcctgtac cacctgctgg       3540
actggtttgc cgtggatgag tccaacgagg tggaccccga gttctctgcc cggctgaccg       3600
gcatcaagct ggagatggag ccttctctga gcttctacaa caaggccaga aattatgcca       3660
ccaagaagcc ctactccgtg gagaagttca gctgaactt tcagatgcct acactggcct       3720
ctggctggga cgtgaataag gagaagaaca tggcgccat cctgtttgtg aagaacggcc       3780
tgtactatct gggcatcatg ccaaagcaga ggggcaggta taaggccctg agcttcgagc       3840
ccacagagaa aaccagcgag ggctttgata agatgtacta tgactacttc cctgatgccg       3900
ccaagatgat cccaaagtgc agcacccagc tgaaggccgt gacagcccac tttcagaccc       3960
```

```
acacaacccc catcctgctg tccaacaatt tcatcgagcc tctggagatc acaaaggaga    4020
tctacgacct gaacaatcct gagaaggagc caaagaagtt tcagacagcc tacgccaaga    4080
aaaccggcga ccagaagggc tacagagagg ccctgtgcaa gtggatcgac ttcacaaggg    4140
attttctgtc caagtatacc aagacaacct ctatcgatct gtctagcctg cggccatcct    4200
ctcagtataa ggacctgggc gagtactatg ccgagctgaa tcccctgctg taccacatca    4260
gcttccagag aatcgccgag aaggagatca tggatgccgt ggagacaggc aagctgtacc    4320
tgttccagat ctataacaag gactttgcca agggccacca cggcaagcct aatctgcaca    4380
cactgtattg gaccggcctg ttttctccag agaacctggc caagacaagc atcaagctga    4440
atggccaggc cgagctgttc taccgcccta agtccaggat gaagaggatg gcacaccggc    4500
tgggagagaa gatgctgaac aagaagctga aggatcagaa aaccccaatc cccgacaccc    4560
tgtaccagga gctgtacgac tatgtgaatc acagactgtc ccacgacctg tctgatgagg    4620
ccagggccct gctgcccaac gtgatcacca aggaggtgtc tcacgagatc atcaaggata    4680
ggcgctttac cagcgacaag ttcttttttcc acgtgcctat cacactgaac tatcaggccg    4740
ccaattcccc atctaagttc aaccagaggg tgaatgccta cctgaaggag cacccccgaga    4800 cacctatcat cggcatcgat cggggcgaga gaaacctgat ctatatcaca gtgatcgact    4860
ccaccggcaa gatcctggag cagcggagcc tgaacaccat ccagcagttt gattaccaga    4920
agaagctgga caacagggag aaggagaggg tggcagcaag gcaggcctgg tctgtggtgg    4980
gcacaatcaa ggatctgaag cagggctatc tgagccaggt catccacgag atcgtggacc    5040
tgatgatcca ctaccaggcc gtggtggtgc tggagaacct gaatttcggc tttaagagca    5100
agaggaccgg catcgccgag aaggccgtgt accagcagtt cgagaagatg ctgatcgata    5160
agctgaattg cctggtgctg aaggactatc agcagagaa agtgggaggc gtgctgaacc    5220
cataccagct gacagaccag ttcacctcct ttgccaagat gggcacccag tctggcttcc    5280
tgttttacgt gcctgcccca tatacatcta agatcgatcc cctgaccggc ttcgtggacc    5340
ccttcgtgtg gaaaaccatc aagaatcacg agagccgcaa gcacttcctg gagggcttcg    5400
actttctgca ctacgacgtg aaaaccggcg acttcatcct gcactttaag atgaacagaa    5460
atctgtcctt ccagagggggc ctgcccggct ttatgcctgc atgggatatc gtgttcgaga    5520
agaacgagac acagtttgac gccaagggca ccccttttcat cgccggcaag agaatcgtgc    5580
cagtgatcga gaatcacaga ttcaccggca gataccggga cctgtatcct gccaacgagc    5640
tgatcgccct gctggaggag aagggcatcg tgttcaggga tggctccaac atcctgccaa    5700
agctgctgga gaatgacgat tctcacgcca tcgacaccat ggtggccctg atccgcagcg    5760
tgctgcagat gcggaactcc aatgccgcca caggcgagga ctatatcaac agccccgtgc    5820
gcgatctgaa tggcgtgtgc ttcgactccc ggtttcagaa cccagagtgg cccatggacg    5880
ccgatgccaa tggcgcctac cacatcgccc tgaaggcca gctgctgctg aatcacctga    5940
aggagagcaa ggatctgaag ctgcagaacg gcatctccaa tcaggactgg ctggcctaca    6000
tccaggagct cgcgcaacaaa aggccggcgg ccacgaaaaa ggccggccag caaaaaaga    6060 aaaagggatc ctacccatac gatgttccag attacgctta tccctacgac gtgcctgatt    6120 atgcatacccc atacgatgtc cccgactatg ccctcgagag caccggtggc agcggagcta    6180
ctaacttcag cctgctgaag caggctggag acgtggagga gaaccctgga cctgccggta    6240
tggtgagcaa gggcgaggag gataacatgg ccatcatcaa ggagttcatg cgcttcaagg    6300
```

-continued

```
tgcacatgga gggctccgtg aacggccacg agttcgagat cgagggcgag ggcgagggcc   6360
gcccctacga gggcacccag accgccaagc tgaaggtgac caagggtggc cccctgccct   6420
tcgcctggga catcctgtcc cctcagttca tgtacggctc caaggcctac gtgaagcacc   6480
ccgccgacat ccccgactac ttgaagctgt ccttccccga gggcttcaag tgggagcgcg   6540
tgatgaactt cgaggacggc ggcgtggtga ccgtgaccca ggactcctcc ctgcaggacg   6600
gcgagttcat ctacaaggtg aagctgcgcg gcaccaactt cccctccgac ggccccgtaa   6660
tgcagaagaa gaccatgggc tgggaggcct cctccgagcg gatgtacccc gaggacggcg   6720
ccctgaaggg cgagatcaag cagaggctga agctgaagga cggcggccac tacgacgctg   6780
aggtcaagac cacctacaag gccaagaagc ccgtgcagct gcccggcgcc tacaacgtca   6840
acatcaagtt ggacatcacc tcccacaacg aggactacac catcgtggaa cagtacgaac   6900
gcgccgaggg ccgccactcc accggcggca tggacgagct gtacaagtaa ctgcagcgcg   6960
gggatctcat gctggagttc ttcgcccacc ccaacttgtt tattgcagct tataatggtt   7020
acaaataaag caatagcatc acaaatttca caaataaagc atttttttca ctgcattcta   7080
gttgtggttt gtccaaactc atcaatgtat cttatcatgt ctgtataccg tcgacctcta   7140
gctagagctt ggcgtaatca tggtcatagc tgtttcctgt gtgaaattgt tatccgctca   7200
caattccaca caacatacga gccggaagca taaagtgtaa agcctagggt gcctaatgag   7260
tgagctaact cacattaatt gcgttgcgct cactgcccgc tttccagtcg ggaaacctgt   7320
cgtgccagct gcattaatga atcggccaac gcgcggggag aggcggtttg cgtattgggc   7380
gctcttccgc ttcctcgctc actgactcgc tgcgctcggt cgttcggctg cggcgagcgg   7440
tatcagctca ctcaaaggcg gtaatacggt tatccacaga atcaggggat aacgcaggaa   7500
agaacatgtg agcaaaaggc cagcaaaagg ccaggaaccg taaaaaggcc gcgttgctgg   7560
cgtttttcca taggctccgc ccccctgacg agcatcacaa aaatcgacgc tcaagtcaga   7620
ggtggcgaaa cccgacagga ctataaagat accaggcgtt tccccctgga agctccctcg   7680
tgcgctctcc tgttccgacc ctgccgctta ccggatacct gtccgccttt ctcccttcgg   7740
gaagcgtggc gctttctcat agctcacgct gtaggtatct cagttcggtg taggtcgttc   7800
gctccaagct gggctgtgtg cacgaacccc ccgttcagcc cgaccgctgc gccttatccg   7860
gtaactatcg tcttgagtcc aacccggtaa gacacgactt atcgccactg gcagcagcca   7920
ctggtaacag gattagcaga gcgaggtatg taggcggtgc tacagagttc ttgaagtggt   7980
ggcctaacta cggctacact agaagaacag tatttggtat ctgcgctctg ctgaagccag   8040
ttaccttcgg aaaaagagtt ggtagctctt gatccggcaa acaaaccacc gctggtagcg   8100
gtggtttttt tgtttgcaag cagcagatta cgcgcagaaa aaaaggatct caagaagatc   8160
ctttgatctt ttctacgggg tctgacgctc agtggaacga aaactcacgt taagggattt   8220
tggtcatgag attatcaaaa aggatcttca cctagatcct tttaaattaa aaatgaagtt   8280
ttaaatcaat ctaaagtata tatgagtaaa cttggtctga cagttaccaa tgcttaatca   8340
gtgaggcacc tatctcagcg atctgtctat ttcgttcatc catagttgcc tgactccccg   8400
tcgtgtagat aactacgata cgggagggct taccatctgg ccccagtgct gcaatgatac   8460
cgcgagaccc acgctcaccg gctccagatt tatcagcaat aaaccagcca gccggaaggg   8520
ccgagcgcag aagtggtcct gcaactttat ccgcctccat ccagtctatt aattgttgcc   8580
gggaagctag agtaagtagt tcgccagtta atagtttgcg caacgttgtt gccattgcta   8640
caggcatcgt ggtgtcacgc tcgtcgtttg gtatggcttc attcagctcc ggttcccaac   8700
```

-continued

```
gatcaaggcg agttacatga tcccccatgt tgtgcaaaaa agcggttagc tccttcggtc    8760
ctccgatcgt tgtcagaagt aagttggccg cagtgttatc actcatggtt atggcagcac    8820
tgcataattc tcttactgtc atgccatccg taagatgctt ttctgtgact ggtgagtact    8880
caaccaagtc attctgagaa tagtgtatgc ggcgaccgag ttgctcttgc ccggcgtcaa    8940
tacgggataa taccgcgcca catagcagaa ctttaaaagt gctcatcatt ggaaaacgtt    9000
cttcggggcg aaaactctca aggatcttac cgctgttgag atccagttcg atgtaaccca    9060
ctcgtgcacc caactgatct tcagcatctt ttactttcac cagcgtttct gggtgagcaa    9120
aaacaggaag gcaaaatgcc gcaaaaaagg gaataagggc gacacggaaa tgttgaatac    9180
tcatactctt cctttttcaa tattattgaa gcatttatca gggttattgt ctcatgagcg    9240
gatacatatt tgaatgtatt tagaaaaata aacaaatagg ggttccgcgc acatttcccc    9300
gaaaagtgcc acctgacgtc gacggatcgg gagatcgatc tcccgatccc ctagggtcga    9360
ctctcagtac aatctgctct gatgccgcat agttaagcca gtatctgctc cctgcttgtg    9420
tgttggaggt cgctgagtag tgcgcgagca aaatttaagc tacaacaagg caaggcttga    9480
ccgac                                                                9485
```

```
<210> SEQ ID NO 6
<211> LENGTH: 34
<212> TYPE: DNA
<213> ORGANISM: Artificial Sequence
<220> FEATURE:
<223> OTHER INFORMATION: The sequence is synthesized

<400> SEQUENCE: 6
accagcgaca agttcttttt ccacgtgcct atca                                34

<210> SEQ ID NO 7
<211> LENGTH: 46
<212> TYPE: DNA
<213> ORGANISM: Artificial Sequence
<220> FEATURE:
<223> OTHER INFORMATION: The sequence is synthesized

<400> SEQUENCE: 7
cacagaccag gcctgagcgg ccgccacctt ctccttctcc ctgttg                   46

<210> SEQ ID NO 8
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 8
gaaggagaag gtggcggccg ctcaggcctg gtctgtggtg ggc                      43

<210> SEQ ID NO 9
<211> LENGTH: 34
<212> TYPE: DNA
<213> ORGANISM: Artificial Sequence
<220> FEATURE:
<223> OTHER INFORMATION: The sequence is synthesized

<400> SEQUENCE: 9
aagcgtaatc tggaacatcg tatgggtagg atcc                                34

<210> SEQ ID NO 10
```

-continued

```
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 10
ctgatggtcc atgtctgtta ctc                                               23

<210> SEQ ID NO 11
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 11
gtgatggtcc atgtctgtta ctc                                               23

<210> SEQ ID NO 12
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 12
ctgatggacc atgtctgtta ctc                                               23

<210> SEQ ID NO 13
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 13
ctgatggtgc atgtctgtta ctc                                               23

<210> SEQ ID NO 14
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 14
ctgatggtcc atgtctgtaa ctc                                               23

<210> SEQ ID NO 15
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 15
ctgatggtcc atgtctgttt ctc                                               23

<210> SEQ ID NO 16
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 16
```

-continued caagtgctta gagcaggcgt                                                    20

<210> SEQ ID NO 17
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 17
gtgacgggag ggcagaacta                                                    20

<210> SEQ ID NO 18
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 18
gggtgatcag acccaacagc agg                                                23

<210> SEQ ID NO 19
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 19
gggtgatcag acccaacacc agg                                                23

<210> SEQ ID NO 20
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 20
gggtgatcag acccaacacc agg                                                23

<210> SEQ ID NO 21
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 21
ccacatcctc accacctgtt                                                    20

<210> SEQ ID NO 22
<211> LENGTH: 18
<212> TYPE: DNA
<213> ORGANISM: Artificial Sequence
<220> FEATURE:
<223> OTHER INFORMATION: The sequence is synthesized

<400> SEQUENCE: 22
cccacagcca tccagctc                                                      18

<210> SEQ ID NO 23
<211> LENGTH: 22
<212> TYPE: DNA

-continued

```
<213> ORGANISM: Artificial Sequence
<220> FEATURE:
<223> OTHER INFORMATION: The sequence is synthesized

<400> SEQUENCE: 23
acactacgat ggtccctggt gc                                             22

<210> SEQ ID NO 24
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 24
tggatgctgg atggcgtcac at                                             22

<210> SEQ ID NO 25
<211> LENGTH: 24
<212> TYPE: DNA
<213> ORGANISM: Artificial Sequence
<220> FEATURE:
<223> OTHER INFORMATION: The sequence is synthesized

<400> SEQUENCE: 25
agccaatatt attacattgc cgtt                                           24

<210> SEQ ID NO 26
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 26
tggcgtcaca ttagtgccat                                                20

<210> SEQ ID NO 27
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 27
gacttggcta gcttggggac                                                20

<210> SEQ ID NO 28
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 28
gctgtgagaa accccatgtt                                                20

<210> SEQ ID NO 29
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 29
gacagttcag acccttgggg                                                20
```

-continued

```
<210> SEQ ID NO 30
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 30
tgctgtgaga aaccccatgt t                                          21
```

CONSTRUCTION OF HIGH-FIDELITY CRISPR/ASCPF1 MUTANT AND USES THEREOF

CROSS REFERENCE TO THE RELATED APPLICATIONS

This application is the national phase entry of International Application No. PCT/CN2019/101439, filed on Aug. 19, 2019, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJCH053_Sequence Listing2.txt, created on Aug. 26, 2022 and is 58,532 bytes in size.

TECHNICAL FIELD

The present invention relates to the field of biotechnology, and in particular to the construction of a high-fidelity CRISPR/AsCpf1 mutant and uses thereof.

BACKGROUND

CRISPR/Cpf1 is a kind of DNA editing technology similar to the CRISPR/Cas9 system; the same as CRISPR/Cas9, CRISPR/Cpf1 belongs to a type-II CRISPR system endonuclease. However, compared with Cas9, Cpf1 is smaller and simpler in structure. Moreover, Cpf1 further has some properties not possessed by Cas9, such as, Cpf1 cleavage forms cohesive ends, the PAM region is TTTN, and Cpf1 has self-processing CrRNA ability by itself. Therefore, Cpf1 can not only help make up for some defects of the CRISPR/Cas9 system, but also is more superior to CRISPR/Cas9 in some aspects of application probably. At present, the CRISPR system has been applied extensively, and particularly applied in the aspects, such as gene therapy of a disease and improvement of degenerative changes gradually. The CRISPR system can perform efficient gene editing on various cells, tissues, organs and the like, but the system will produce non-targeted cleavage in the position similar to a target site sequence; this is the so-called "off-target effect". The off-target effect will cause some unpredictable mutations such that there probably exists a potential risk if these nucleases are applied to clinical practice. Based on this, it is very crucial to develop a high-fidelity CRISPR system. Currently, several versions have been developed to the high-fidelity Cas9, such as, eCas9, Cas9-HF, HypaCas9 and evoCas9. But for Cpf1, rare high-fidelity version has been developed currently. Therefore, based on the point mutation technology, an efficient novel Cpf1 mutant capable of lowering the off-target effect is found in this prevent invention by a series of mutation transformations.

SUMMARY

The first objective of the prevent invention is to provide a novel AsCpf1 mutant (AsCpf1-KA mutant) with reduced off-target effect, namely, a high-fidelity CRISPR/AsCpf1 mutant.

To achieve the above objective, the technical solution adopted in the prevent invention is an AsCpf1 mutant; and the AsCpf1 mutant is obtained by performing a mutation on arginine at position 951 of the AsCpf1 protein amino acid sequence and replacing the same with an amino acid free of forming a hydrogen bond with the target site DNA;

or an AsCpf1 mutant is obtained by performing a mutation on arginine at position 955 of the AsCpf1 protein amino acid sequence and replacing the same with an amino acid free of forming a hydrogen bond with DNA of a target site;

or an AsCpf1 mutant is obtained by performing mutations on arginines at positions 951 and 955 of the AsCpf1 protein amino acid sequence and replacing the same with amino acids free of forming a hydrogen bond with DNA of a target site.

Further, the AsCpf1 mutant is obtained by performing mutations on arginines at positions 951 and 955 of the AsCpf1 protein amino acid sequence and replacing the same with aminos acid free of forming a hydrogen bond with DNA of a target site.

Further, the AsCpf1 mutant is obtained by mutating arginine at position 951 of the AsCpf1 protein amino acid sequence into lysine; and the AsCpf1 mutant has an amino acid sequence as shown in SEQ ID NO: 1;

or the AsCpf1 mutant is obtained by mutating arginine at position 955 of the AsCpf1 protein amino acid sequence into alanine; and the AsCpf1 mutant has an amino acid sequence as shown in SEQ ID NO: 2;

or the AsCpf1 mutant is obtained by mutating arginine at position 951 of the AsCpf1 protein amino acid sequence into lysine and arginine at position 955 thereof into alanine; and the AsCpf1 mutant has an amino acid sequence as shown in SEQ ID NO: 3.

Further, the AsCpf1 mutant is obtained by mutating arginine at position 951 of the AsCpf1 protein amino acid sequence into lysine (951R->K) and arginine at position 955 thereof into alanine (955R->A); and the AsCpf1 mutant has an amino acid sequence as shown in SEQ ID NO: 3.

In 2016, Feng Zhang group analyzed a three-dimensional structure of AsCpf1 protein (derived from a common bacterial genus in the Cpf1 family). Through research and analysis, the applicant has found that amino acids R at position 951 and 955 of AsCpf1 can form nonspecific hydrogen bonding with the target site DNA of the genome, which may cause that AsCpf1 will form nonspecific binding at some positions similar to target site sequences during gene editing, thereby producing non-targeted cleavage. Therefore, the applicant performs mutations on these positions to break the nonspecific hydrogen bonding between the protein and the target site, such that AsCpf1 demands for stronger complementary pairing between gRNA and the target site during gene editing, thus reducing the off-target effect.

The second objective of the prevent invention is to provide an encoding gene of the AsCpf1 mutant mentioned above.

To achieve the above objective, the technical solution adopted in the prevent invention is an encoding gene of the AsCpf1 mutant mentioned above; the nucleotide sequence thereof is shown in SEQ ID NO: 4.

The third objective of the prevent invention is to provide use of the encoding gene mentioned above in the construction of a CRISPR/AsCpf1 gene editing system. The fourth objective of the prevent invention is to provide a CRISPR/AsCpf1 gene editing system.

To achieve the above objective, the technical solution adopted in the prevent invention is a CRISPR/AsCpf1 gene editing system, including a gene encoding a AsCpf1 protein, and the AsCpf1 protein is the AsCpf1 mutant mentioned above.

Further, the CRISPR/AsCpf1 gene editing system further includes a U6 promoter used for initiating the sgRNA expression of the encoding gene of the AsCpf1 mutant, a necessary element crRNA for AsCpf1 gene editing, a eukaryotic promoter CAG used for initiating the expression of the encoding gene of the AsCpf1 mutant, a cleaving peptide sequence P2A, and a reporter gene mCherry for monitoring plasmid expression. The specific effects are as follows:

1. U6 promoter serves to initiate the sgRNA expression of the AsCpf1 mutant gene;
2. AsCpf1 scaffold, namely, crRNA, is one of necessary elements of AsCpf1 gene editing, and also is an element guiding a target sequence;
3. eukaryotic promoter CAG serves to initiate the expression of the AsCpf1 mutant gene;
4. cleaving peptide sequence P2A is a protein flexible linker sequence;
5. gene of red fluorescence protein mCherry is a fluorescent reporter gene.

As specificity verification, site3 of DNMT1 (DNA transmethylase 1) and another Match-site6 are selected in the examples herein. Two methods, namely, mismatched bases of target gRNA and known off-target sites of target gRNA are taken. Common genotyping methods PAGE and T7E1 are taken in technical aspect; the wild-type AsCpf1 plasmid (pu6-CAG-AsCpf1-mCherry wild-type AsCpf1 plasmid) and AsCpf1 mutant plasmid (pu6-CAG-AsCpf1-KA-mCherry mutant AsCpf1-KA plasmid) are transfected in HEK-293T (human kidney epithelial cell line) and MCF7 (human breast cancer cell line) for verification. It is proved by the results that the mutative AsCpf1 mutant (AsCpf1-KA) has better specificity than that of the wild-type AsCpf1 either at mismatched bases or known off-target sites, and in different cell lines 293T or MCF7.

The fifth objective of the prevent invention is to provide use of the CRISPR/AsCpf1 gene editing system mentioned above in reducing off-target effect in gene editing.

Compared with the prior art, the prevent invention has the following advantages:

The gene editing off-target efficiency of the AsCpf1-KA mutant (namely AsCpf1 mutant) provided by the prevent invention is far below that of the wild-type AsCpf1. PAGE and T7E1 results show that the cleavage (off-target cleavage) efficiency is far below that of the wild-type either at a DNMT1-Site3 where gRNA is incompletely matched to the target site or at a completely matched Match-site6. Moreover, it can be obviously observed that the AsCpf1-KA has better fidelity and can reduce 2 known off-target sites of the Match-site6 below the limit of detection in different cell lines (293T or MCF7 cell line). The above results indicate that the AsCpf1-KA mutant not only has better targeted cleavage activity, but also has better specificity than the wild-type AsCpf1 and thus, is a high-fidelity CRISPR nuclease.

DETAILED DESCRIPTION OF THE EMBODIMENTS

The prevent invention will be further described in combination with the detailed examples, but the prevent invention is not limited to the following examples. Unless otherwise specified, the technologies used in the following examples are conventional technologies known by a person skilled in the art; the instrument and equipment, reagents and the like used are obtained by a person skilled in the art via public approaches, e.g., commercial purchase.

EXAMPLE 1

Construction of a Recombinant Expression Plasmid

The pU6-CAG-AsCpf1-mCherry sequence is shown in SEQ ID NO: 5.

Figures 1, 2:
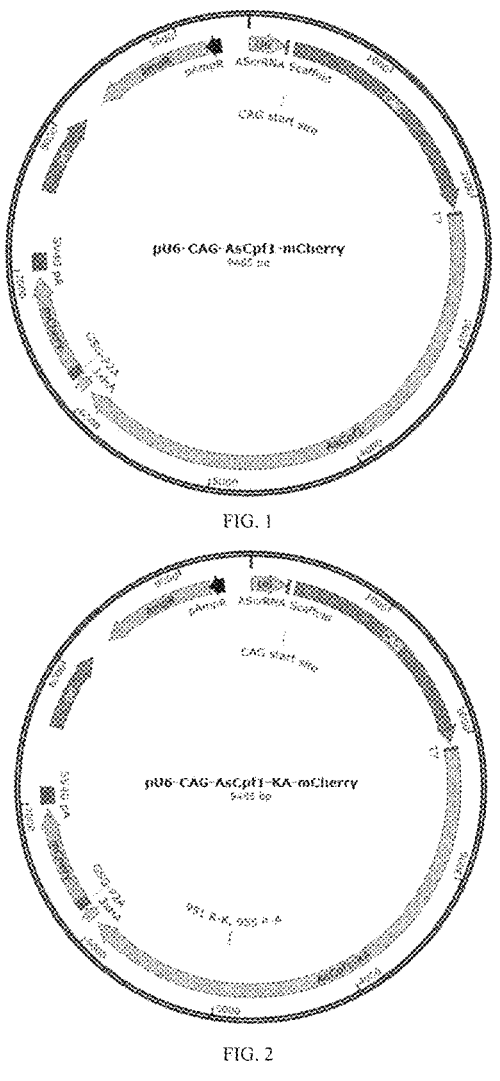
FIG. 1 shows a plasmid profile of a pU6-CAG-AsCpf1-mCherry wild-type AsCpf1.
FIG. 2 shows a plasmid profile of a pU6-CAG-AsCpf1-KA-mCherry mutant AsCpf1-KA.

The wild-type pU6-CAG-AsCpf1-mCherry (FIG. 1) served as a vector (the nucleotide sequence thereof is shown in SEQ ID NO: 5), and the Gibson Assembly® principle and technology was used to design the corresponding mutation primers for PCR, and finally ligation was performed to obtain pU6-CAG-AsCpf1-KA-mCherry (FIG. 2). Specific steps were as follows:

The pU6-CAG-AsCpf1-mCherry vector was firstly subjected to PmI I and BamHI enzyme digestion to obtain a backbone vector. The pU6-CAG-AsCpf1-mCherry served as a template and PCR amplification was performed respectively to obtain fragments containing mutation bases. The PCR primer sequences are as follows:

```
AsCpf1-Pml I-F:
                                    (SEQ ID NO: 6)
5'-ACCAGCGACAAGTTCTTTTTCCACGTGCCTATCA-3';

AsCpf1-KA-R:
                                    (SEQ ID NO: 7)
5'-CACAGACCAGGCCTGAGCGGCCGCCACCTTCTCCTTCTCCCTGTTG-
3';

AsCpf1-KA-F:
                                    (SEQ ID NO: 8)
5'-GAAGGAGAAGGTGGCGGCCGCTCAGGCCTGGTCTGTGGTGGGC-3';

AsCpf1-BamH I-R:
                                    (SEQ ID NO: 9)
5'-AAGCGTAATCTGGAACATCGTATGGGTAGGATCC-3'.
```

A plasmid pU6-CAG-AsCpf1-mCherry served as a template and NEB Q5 enzyme was used for PCR (50 µl system was as follows: 10 µl 5×reaction buffer; 10 µl 5×enhance GC buffer; 4 µl dNTP Mix 2.5 µm each; 2+2 µl F+R; Template: 2 ng DNA; water: up to 50 µl. Reaction conditions were as follows: the reaction was performed for 15 s at 98° C., and 35 cycles were performed (10 s at 98° C., 30 s at 58° C. and 1 kb/s at 72° C.), 10 min at 72° C., and hold at 4° C.), then electrophoresis was performed to obtain a single product, and a PCR purification kit was used for purification.

AsCpf1-Pml I-F and AsCpf1-KA-R were subjected to PCR; the product was named PCR-fragment 1;

AsCpf1-KA-F and AsCpf1-Bam H I-R were subjected to PCR; the product was named PCR-fragment 2;

The PCR fragment 1, PCR fragment 2 and a backbone vector fragment 3 which was obtained by performing double enzyme digestion on the pU6-CAG-AsCpf1-mCherry vector with restriction enzymes PmI I and BamHI were subjected to Gibson Assembly® reaction with a Gibson Assembly® kit, thus obtaining a target plasmid pU6-CAG-AsCpf1-KA-mCherry (FIG. 2). The plasmid was only used to mutate arginine R at position 951 on the amino acid sequence of the AsCpf1 protein in the pU6-CAG-AsCpf1-mCherry vector into lysine K (951R->K), and to mutate arginine R at position 955 thereof into alanine A (955R->A); and the mutated AsCpf1 mutant has an amino acid sequence as shown in SEQ ID NO: 3.

EXAMPLE 2

Specific Verification

To verify the better fidelity of the obtained mutant AsCpf1-KA (namely, AsCpf1 mutant) than the wild-type AsCpf1, the following experiment was designed for specificity verification:

(1) It has been reported in the literature (B P Kleinstiver, et al. Genome-wide specificities of CRISPR-Cas Cpf1 nucleases in human cells, Nature. 2016) that the wild-type AsCpf1 can also perform cleavage on some incompletely matched gRNA, in particular to positions 1, 2, 8, 9, 19, 20, 21, 22, and 23. That is, some gRNA base mismatches are allowed by the wild-type AsCpf1, namely, the specificity is ordinary. Therefore, by reference to the literature, gRNA directed to such a site of DNMT1-site3 was designed for verification, including gRNA at positions, such as the completely matched target site (ON), mismatched 1 (mm1), mismatched 8 (mm8), mismatched 9 (mm9), mismatched 19 (mm19), mismatched 20 (mm20). The specific sequence is as follows:

```
AsCpf1-gRNA-DNMT1-3-ON:
                          (SEQ ID NO: 10)
CTGATGGTCCATGTCTGTTACTC;

AsCpf1-gRNA-DNMT1-3-mm1:
                          (SEQ ID NO: 11)
GTGATGGTCCATGTCTGTTACTC
(the underline represents
the mismatched position);

AsCpf1-gRNA-DNMT1-3-mm8:
                          (SEQ ID NO: 12)
CTGATGGACCATGTCTGTTACTC
(the underline represents
the mismatched position);

AsCpf1-gRNA-DNMT1-3-mm9:
                          (SEQ ID NO: 13)
CTGATGGTGCATGTCTGTTACTC
(the underline represents
the mismatched position);
```

6

-continued

```
AsCpf1-gRNA-DNMT1-3-mm19:
                          (SEQ ID NO: 14)
CTGATGGTCCATGTCTGTAACTC
(the underline represents
the mismatched position);

AsCpf1-gRNA-DNMT1-3-mm20:
                          (SEQ ID NO: 15)
CTGATGGTCCATGTCTGTTTCTC
(the underline represents
the mismatched position).
``` pU6-pCAG-AsCpf1-mCherry and pU6-pCAG-AsCpf1-KA-mCherry respectively served as vectors, and BaeI enzyme digestion was performed to obtain a 9452 bp vector, thus synthesizing the corresponding gRNA-oligo-F and R; then the gRNA-oligo-F and R were annealed to obtain DNA sequences of gRNA; the vectors were linked to the completely matched or mismatched gRNA with a T4 ligase kit, thereby obtaining the plasmid:

pU6-CAG-AsCpf1-mCherry-ON (namely, pU6-CAG-AsCpf1-mCherry was linked to AsCpf1-gRNA-DNMT1-3-ON, and so on), pU6-CAG-AsCpf1-mCherry-mm1, pU6-CAG-AsCpf1-mCherry-mm8, pU6-CAG-AsCpf1-mCherry-mm9, pU6-CAG-As-Cpf1-mCherry-mm19, pU6-CAG-AsCpf1-mCherry-mm20; pU6-CAG-AsCpf1-KA-mCherry-ON, pU6-CAG-AsCpf1-KA-mCherry-mm1, pU6-CAG-AsCpf1-KA-mCherry-mm8, pU6-CAG-AsCpf1-KA-mCherry-mm9, pU6-CAG-AsCpf1-KA-mCherry-mm19, and pU6-CAG-AsCpf1-KA-mCherry-mm20;

the above constructed 12 expression plasmids were transfected into HEK293T with a transfection reagent PEI, 48 h later, cells were digested, and genome DNA was extracted by a SDS pyrolysis method; then the genome DNA served as a template for PCR amplification. The primers are as follows:

```
DNMT1-3-PAGE-F:
                          (SEQ ID NO: 16)
5'-CAAGTGCTTAGAGCAGGCGT-3';

DNMT1-3-PAGE-R:
                          (SEQ ID NO: 17)
5'-GTGACGGGAGGGCAGAACTA-3'.
```

The PCR reaction system was as follows:
gDNA: 50 ng; F+R primer: 0.5 μl; 2× PCR mix: 5 μl; water: up to 10 μl.

The reaction conditions were as follows: the reaction was performed for 5 min at 95° C., 40 cycles were performed (30 s at 95° C., 30 s at 58° C. and 20 s at 72° C.), 10 min at 72° C. and 5 min at 95° C.; then natural cooling was performed to room temperature.

Figure 3:
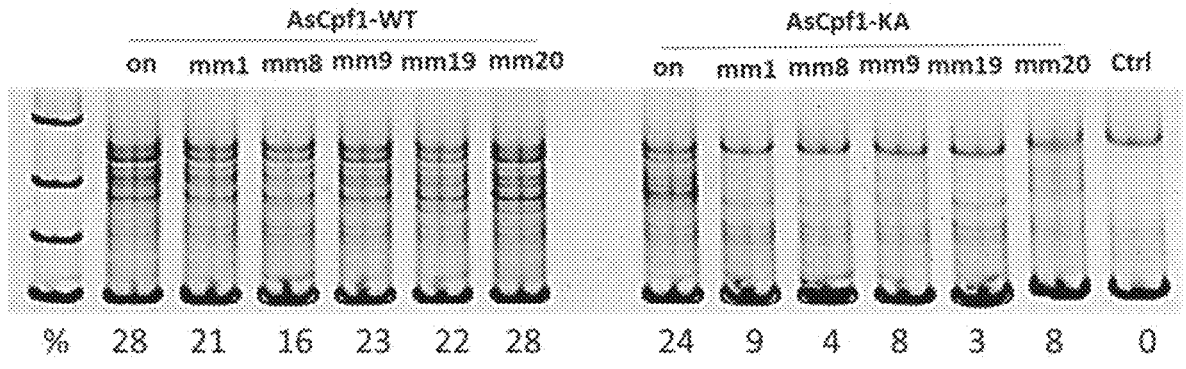
FIG. 3 shows a PAGE gel diagram of the targeted gRNA and mismatched gRNA of the wild-type AsCpf1 (AsCpf1-WT) and AsCpf1-KA (namely, AsCpf1 mutant) at DNMT1-site3.

1) 2 μl PCR product was taken for sampling, then PAGE electrophoresis was performed at a constant current of 12 m Ah, when bromophenol blue bands moved to a position in front of about 1 cm away from the gel, the electrophoresis was stopped;

2) after reaching the time point, the PAGE gel was slightly striped from the glass plate, and then put to a GelRed®-containing solution for soaking for 3 min, and the soaked PAGE gel was photographed under ultraviolet light and observed;

3) the PAGE gel was subjected to genotype identification to observe the editing efficiency and specificity conditions. The results are shown in FIG. 3. The results indicate that for the wild-type AsCpf1, an obvious cleavage effect (obvious hybrid bands appeared; particularly, the mismatch at position 20 displayed 28% editing efficiency basically the same with the matched gRNA) can be also detected by using the mismatched gRNA (positions 1, 8, 9, 19 and 20); while for the modified AsCpf1-KA, the cleavage effect detected by the mismatched gRNA (positions 1, 8, 9, 19 and 20) is obviously lower than that of the wild-type, and basically keeps below 10% and meanwhile maintains the efficiency almost the same with the wild-type (28%), being up to 24% editing efficiency.

(2) Moreover, it is reported in the literature that the wild-type AsCpf1 has obvious off-target sites on Match-site6. Therefore, the applicant picked out 2 of them for verification. Positions and sequences of the targeted gRNA and 2 off-target gRNA are as follows:

```
Chr3: Match-site6-ON:
                            (SEQ ID NO: 18)
GGGTGATCAGACCCAACAGCAGG;

Chr2: Match-site6-OT1:
                            (SEQ ID NO: 19)
GGGTGATCAGACCCAACACCAGG
(the underline represents
the mismatched position);
```

Chr8: Match-site6-OT2: GGGTGATCAGACC-CAACACCAGG (the underline represents the mismatched position) (SEQ ID NO: 20).

Similarly, pU6-pCAG-AsCpf1-mCherry and pU6-pCAG-AsCpf1-KA-mCherry respectively served as vectors, and BaeI enzyme digestion was performed to obtain a 9452 bp vector, thus synthesizing the targeted gRNA-oligo-F and R; then the targeted gRNA-oligo-F and R were annealed to obtain DNA sequences of site6-ON-gRNA; the vectors were linked to the DNA sequences of gRNA with a T4 ligase kit, thereby obtaining the plasmid:

pU6-CAG-AsCpf1-mCherry-site6-ON pU6-CAG-AsCpf1-KA-mCherry-site6-ON

The above constructed 2 expression plasmids were transfected into HEK293T or MCF7 with a transfection reagent PEI, 48 h later, cells were digested, and genome DNA was extracted by a SDS pyrolysis method; then the genome DNA served as a template for PCR amplification, and T7E1 and PAGE gels were applied for editing efficiency and specificity analysis. The primers used are as follows:

```
Site6-ON-F:
                            (SEQ ID NO: 21)
5'-CCACATCCTCACCACCTGTT-3';

Site6-ON-R:
                            (SEQ ID NO: 22)
5'-CCCACAGCCATCCAGCTC-3';

Site6-OT1-PAGE-F:
                            (SEQ ID NO: 23)
5'-ACACTACGATGGTCCCTGGTGC-3';

Site6-OT1-PAGE-R:
                            (SEQ ID NO: 24)
5'-TGGATGCTGGATGGCGTCACAT-3';

Site6-OT1-T7E1-F:
                            (SEQ ID NO: 25)
5'-AGCCAATATTATTACATTGCCGTT-3';
```

-continued
```
Site6-OT1-T7E1-R:
                            (SEQ ID NO: 26)
5'-TGGCGTCACATTAGTGCCAT-3';

Site6-OT2-PAGE-F:
                            (SEQ ID NO: 27)
5'-GACTTGGCTAGCTTGGGGAC-3';

Site6-OT2-PAGE-R:
                            (SEQ ID NO: 28)
5'-GCTGTGAGAAACCCCATGTT-3';

Site6-OT2-T7E1-F:
                            (SEQ ID NO: 29)
5'-GACAGTTCAGACCCTTGGGG-3';

Site6-OT2-T7E1-R:
                            (SEQ ID NO: 30)
5'-TGCTGTGAGAAACCCCATGTT-3'.
```

The specific T7E1 identification method is as follows:
1) cell genome DNA was extracted;
2) 50 ng gDNA was taken as a template for PCR amplification; and the system was as follows: gDNA: 50 ng; F+R primer: 2 µl; 2× PCR mix: 15 µl; water: up to 30; the reaction conditions were as follows: the reaction was performed for 5 min at 95° C., 38 cycles were performed (30 s at 95° C., 30 s at 58° C. and 20 s at 72° C.), 10 min at 72° C. and Hold at 4° C.;
3) the PCR product was purified, and then 300 ng DNA was taken for annealing;
DNA purification: 300 ng; NEB buffer 2: 2 ul; water: up to 20 µl;
the reaction conditions were as follows: the reaction was performed for 5 min at 95° C., then natural cooling was performed to room temperature, then 0.3 µl T7E1 incision enzyme was added for reacting for 4 h at 37° C., and electrophoresis was performed, then photographing and observation were performed under ultraviolet light.

The specific PAGE gel identification method is as follows:
1) cell genome DNA was extracted;
2) 50 ng gDNA was taken as a template for PCR amplification; and the system was as follows: gDNA: 50 ng; PAGE-F+R primer: 0.5 µl; 2× PCR mix: 5 µl; water: up to 10;

The reaction conditions were as follows: the reaction was performed for 5 min at 95° C., 40 cycles were performed (30 s at 95° C., 30 s at 58° C. and 20 s at 72° C.), 10 min at 72° C. and 5 min at 95° C.; then natural cooling to room temperature;
3) 2 µl PCR product was taken for loading, and PAGE electrophoresis was performed at a constant current of 12 m Ah, when bromophenol blue bands moved to a position in front of about 1 cm away from the gel, the electrophoresis was stopped;
4) after reaching the time point, the PAGE gel was slightly striped from the glass plate, and then put to a GelRed®-containing solution for soaking for 3 min, and the soaked PAGE gel was photographed under ultraviolet light and observed.

Figure 4:
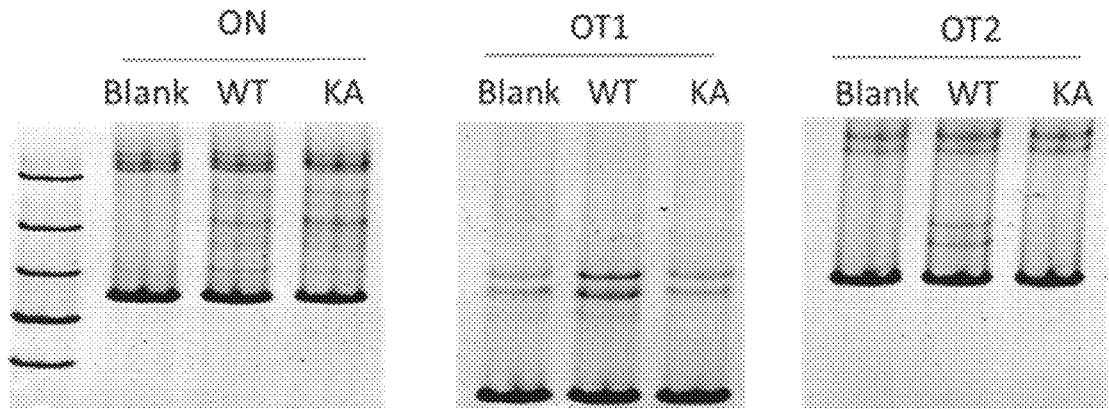
FIG. 4 shows a PAGE gel diagram of the targeted gRNA and 2 off-target sites of the wild-type AsCpf1 and AsCpf1 mutant at Match-site6, where, Blank represents blank control, WT represents the wild-type AsCpf1 and KA represents the AsCpf1-KA mutant.
Figure 5:
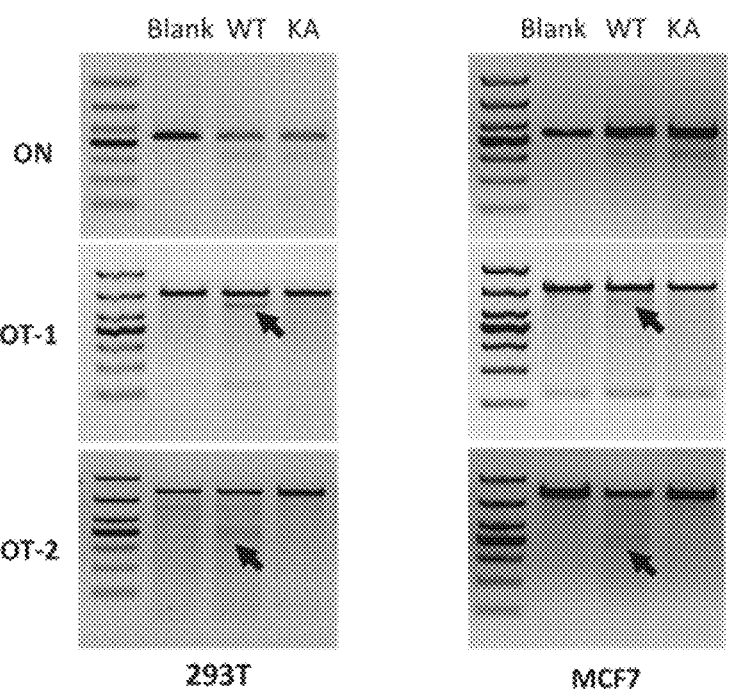
FIG. 5 shows a T7E1 gel diagram of the targeted gRNA and 2 off-target sites of the wild-type AsCpf1 and AsCpf1 mutant at Match-site6, wherein, Blank represents blank control, WT represents the wild-type AsCpf1 and KA represents the AsCpf1-KA mutant. (Left: cell line HEK293T, right: cell line MCF7; the black arrows represent the off-target cleavage conditions)

The editing efficiency and specificity conditions displayed by the PAGE gel and T7E1 are shown in FIGS. 4 and 5. The results are consistent with the expected value, that is, the gene editing off-target efficiency of the mutant AsCpf1-KA is far below that of the wild-type AsCpf1. PAGE and T7E1 results show that the cleavage (off-target cleavage) efficiency is far below that of the wild-type either at a DNMT1-

Site3 where gRNA is incompletely matched to the target site or at a completely matched Match-site6. Moreover, it can be obviously observed that the mutant AsCpf1-KA has better fidelity and may reduce 2 known off-target sites of the Match-site6 below the limit of detection in different cell lines (293T or MCF7 cell line), shown by the black arrows. All of these results indicate that the AsCpf1-KA mutant not only has better targeted cleavage activity, but also has better specificity than the wild-type AsCpf1 and thus, is a high-fidelity CRISPR nuclease.

What is described above are merely preferred embodiments of the present invention. It should be indicated that the above preferred embodiments should be not construed as limiting the prevent invention; and the protection scope of the prevent invention should be subject to the scope defined by the claims. A person skilled in the art may further make several improvements and embellishments within the spirit and scope of the present invention, and these improvements and embellishments shall fall within the protection scope of the present invention.

What is claimed is:

1. An AsCpf1 mutant comprising SEQ ID NO: 1 or SEQ ID NO: 3.

2. A nucleotide sequence encoding an AsCpf1 mutant having SEQ ID NO: 1 or SEQ ID NO: 3.

3. A method of constructing a CRISPR/AsCpf1 gene editing system, comprising a step of cloning the nucleotide sequence of claim 2 into an expression vector.

4. The method according to claim 3, wherein the nucleotide sequence encoding the AsCpf1 mutant comprises SEQ ID NO: 4.

5. A CRISPR/AsCpf1 gene editing system, comprising the nucleotide sequence of claim 2.

6. The CRISPR/AsCpf1 gene editing system according to claim 5, wherein the CRISPR/AsCpf1 gene editing system further comprises:

(a) a U6 promoter for initiating expression of a crRNA;
(b) a eukaryotic promoter for initiating expression of the AsCpf1 mutant; and (c) a splicing peptide sequence P2A positioned downstream of the nucleic acid sequence encoding the AsCpf1 mutant and under the control of the eukaryotic promoter.

7. A method of reducing off-target effect of gene editing in a cell, comprising a step of introducing into the cell the CRISPR/AsCpf1 gene editing system according to claim 5 for the gene editing.

8. The method according to claim 7, wherein the CRISPR/AsCpf1 gene editing system further comprises:

(a) a U6 promoter for initiating expression of a crRNA;
(b) a eukaryotic promoter for initiating expression of the AsCpf1 mutant; and
(c) a splicing peptide sequence P2A positioned downstream of the nucleic acid sequence encoding the AsCpf1 mutant and under the control of the eukaryotic promoter.

* * * * *